US006033365A

United States Patent [19]

von Zitzewitz

[11] Patent Number: 6,033,365

[45] Date of Patent: Mar. 7, 2000

[54] EQUIPMENT FOR RECORDING A PATIENT'S STATE OF HEALTH

[76] Inventor: Falk von Zitzewitz, Vorsteigstrasse 15, D-70193 Stuttgart, Germany

[21] Appl. No.: 09/125,793

[22] PCT Filed: Apr. 7, 1997

[86] PCT No.: PCT/EP97/01712

§ 371 Date: Aug. 31, 1998

§ 102(e) Date: Aug. 31, 1998

[87] PCT Pub. No.: WO97/37585

PCT Pub. Date: Oct. 16, 1997

[30] Foreign Application Priority Data

Apr. 11, 1996 [DE] Germany ........................... 196 14 255

[51] Int. Cl.[7] ............................ A61B 5/00; G04B 47/00; G06F 3/02

[52] U.S. Cl. ........................................ 600/300; 128/897

[58] Field of Search ............................ 600/300; 128/897, 128/898, 920

[56] References Cited

U.S. PATENT DOCUMENTS 4,975,842 12/1990 Darrow et al. .

5,653,739 8/1997 Maurer et al. ............................ 607/46

FOREIGN PATENT DOCUMENTS 2 599 252 12/1987 France .

37 03 404 8/1988 Germany .

40 25 830 5/1991 Germany .

WO 94/06088 3/1944 WIPO .

WO 96/25877 8/1996 WIPO .

*Primary Examiner*—Eric F. Winakur

*Attorney, Agent, or Firm*—Foley & Lardner

[57] ABSTRACT

A portable device for recording a patient's state of health is described which measures and records the subjective state of health of a patient. With this device the patient himself records the variation in the effect of medication with time by pressing buttons on mobile equipment and stores this data on a recording medium. This equipment (1) has buttons by means of which the patient can enter the time at which the medication was taken and the time and value of any positive or negative effect. This variation in the effect with time is recorded and can be output via a chip and thus reproduced.

23 Claims, 3 Drawing Sheets

EQUIPMENT FOR RECORDING A PATIENT'S STATE OF HEALTH

FIELD OF THE INVENTION

The invention relates to portable equipment for recording, displaying and storing subjective values concerning a patient's state of health. More particularly, the invention relates to portable equipment, such as a portable computer, for recording, displaying and storing values input by a patient himself.

BACKGROUND OF THE INVENTION

It is known to record certain physiological values of a patient by means of measurement equipment or sensors which can be worn on the body, and to store these values on a recording medium in recording equipment. Thus, for example, changes in a patient's blood pressure can be measured and recorded over the course of time. The measurement is effected by means of suitable measurement equipment, that is to say automatically without any action on the part of the patient. It is also known to use special measurement equipment to detect and record a patient's hand movements in terms of their amplitude in order in this way to obtain a reliable picture of the pattern of movement over the course of time. Finally, oxygen meters for continuously measuring the oxygen content of a patient's blood in respiratory distress and apnea syndrome are also known. These apparatus fail in cases where it is a matter of recording physiological values which cannot be easily measured physically. In such cases, the doctor has to rely on questioning the patient about his state of health and about the effect of the medication. Since the answers given by the patient are based on memory, experiences are often distorted and wrong assessments and inaccurate data are often given, which are therefore of only limited use, if any, to the doctor.

A pocket computer for recording a patient's data has already been disclosed in DE-A-37 03 404. In this, the patient inputs subjective parameters concerning his state of health into the equipment at certain times which are set by a program, and the equipment stores the data with the clock time and the date. Using control buttons, the patient can set the cursor on a scale in such a way that the degree of his subjective symptoms is marked and then stored. This equipment and the data recorded with it have no reference whatsoever to the time at which the medication was taken by the patient.

A battery-operated miniaturized computer for collecting outpatient data has been disclosed in DE-A-40 25 830, in which the patient, after a complicated cycle of questions, assesses his state of health subjectively and inputs this assessment by means of buttons into the equipment and stores it. This data interrogation and input also has only an indirect reference to the time at which medication is taken. In addition, the input values are without reference to the previous value, i.e. "absolute". The patient cannot see the value he last entered, and must therefore carry out an absolute new assessment at the time in question. There is therefore no coherent and meaningful picture of the changes in the state of health over the course of time.

WO 94/06088 disclosed a process which, by means of a portable computer, gives the patient advice on when and how to take medication. The patient himself inputs various data, which he is asked for by the computer, into the equipment and this data is processed and used to give instructions on the administration of medication in terms of dose and time, and in addition to this an expert system is consulted which finally issues the recommendation binding on the patient. To this extent, this process represents a "closed loop" between patient and computer, in which the computer obviously assumes the role of the doctor. Such a process, and the equipment necessary for carrying out this process, are very elaborate and complicated and are therefore not always suitable for patients whose faculty of perception and mobility are impaired. In addition, the recommendations given by such a "computer doctor" must of course be qualified since such equipment cannot take the place of the actual doctor.

SUMMARY OF THE INVENTION

The object of the invention is to make available equipment for recording physiological values that cannot be measured objectively, or the state of health of a patient, with respect to medication the patient is taking, in particular a patient whose faculty of perception and/or motor mobility are limited. According to the invention, this object is achieved by means of a portable device for recording, displaying and storing values concerning a patient's subjective state of health. The portable device comprises a first button for recording a time ($t_0$) at which medication was taken, a second button for recording a positive effect and a time ($t_1$) at which the positive effect is perceived, a third button for recording a negative effect and a time ($t_2$) at which the negative effect is perceived, and a recording medium which stores values input with the first, second, and third buttons.

According to one aspect of the invention, the recording medium is removable from the portable device.

According to another aspect of the invention, there is provided an interface for a PC adapter through which stored data can be transferred from the portable device to a PC.

According to another aspect of the invention, the portable device includes a visual display. This display may be used to display an amount of time elapsed from when medication was taken, the time of day medication was taken, and/or the state of the patient's health. This display may be activated using a fourth button provided on the portable device.

According to another aspect of the invention, activation of the buttons provided on the device may be confirmed acoustically, by touch, or visually.

According to still another aspect of the invention, the portable device includes a speech module including a speaker that provides an audible spoken confirmation of each entry made with the buttons. The speaker may also be used to provide an audible indication of preset times at which medication is to be taken. Alternatively, such preset times may be indicated visually or by vibration of the portable device.

According to still another aspect of the invention, the device further includes a keyboard for recording additional information, such as side effects or feelings experienced by the patient.

According to yet another aspect of the invention, the device may be adapted to be worn around a patient's wrist.

According to still another aspect of the invention, the device further includes a sensor for detecting and recording physically measurable physiological values.

According to another aspect of the invention, the device may be connected to a medication dispenser containing medication to be dispensed at preset times in an appropriate dose.

Using the equipment according to the invention, it is possible to record the subjective state of health of the patient, in particular after taking medication, and with this being done by the patient himself. In this way, the variation in effect, i.e. the change in the effect of medication over the course of time, is recorded on a recording medium and can thus be viewed by the treating physician. By means of this reproducible recording, it is possible to optimize the medication, especially in the case of medication with only a short duration of action. The aim here is to achieve a more uniform effect of the medication for the patient, to avoid side effects caused by overdosage, and to assist the patient by ensuring that medication is taken at the correct time, e.g. in Parkinson's disease. In addition, the patient himself has the advantage that by recording the intensity of the effect and any possible side effects after taking the medication, he can better evaluate the effect. Moreover, this equipment increases the patient's readiness to cooperate constructively with the doctor (so-called compliance). Finally, this equipment can also be used to advantage when carrying out tests and trials on new active substances, drugs and treatment procedures (e.g. clinical trials of medicaments, natural healing processes, irradiation and the like) in order to determine the variations in effect much more accurately. By means of the equipment according to the invention, i.e. by means of the apparatus in the size of a cigarette pack or wristwatch, which can be operated by the patient and is very comfortable to wear, it is possible in a simple manner to record and store a patient's subjective state of health after taking medication. That is, it is possible to record and store the subjective effect of the medication which, for example, is in the form of an instruction for a drug to be taken at certain times, or also in different drug compositions (in respect of amount and type of active substance). It is also possible to enter into the equipment, by means of buttons, the changes in effect over the course of time. At the end of such recording, which can be repeated as often as one likes and by simple pressing of buttons, the recorded values are stored as a function on a recording medium which can be removed from the equipment as a chip or can be transferred directly to analysis equipment (e.g. a PC) via an adapter. This chip, or the display of data on the screen, is used by the treating physician or therapist as a means of checking the effect of medication and at the same time instructs the patient when to take the medication.

BRIEF DESCRIPTION OF THE DRAWINGS

The invention is described in detail below on the basis of a number of illustrative embodiments and is also represented as equipment in the drawing, in which.

DETAILED DESCRIPTION OF PREFERRED EMBODIMENTS

Figure 1:
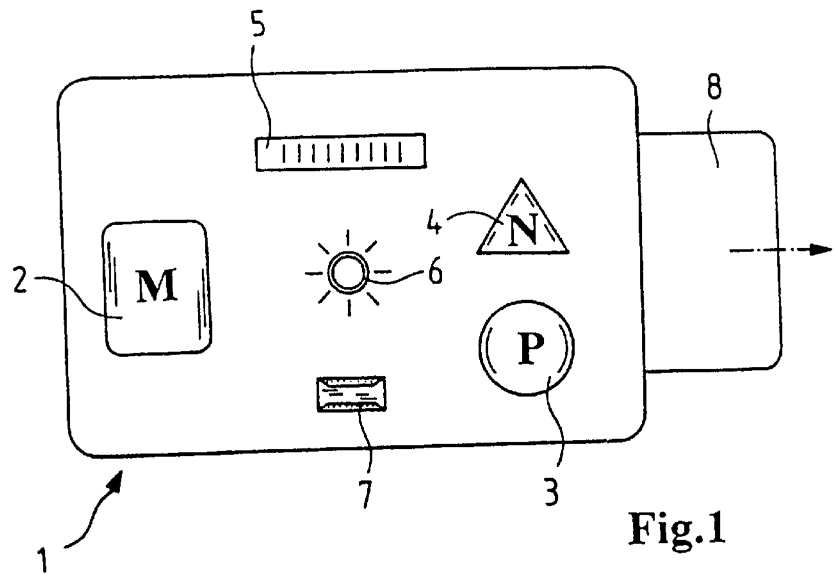
FIG. 1 shows a simplified design of the portable recording equipment.

FIG. 1 shows the recording equipment 1 which can be worn on the patient's body and which is approximately the size of a wristwatch or pocket calculator. This equipment has, on its front side as shown in the drawing, three buttons 2, 3 and 4 which are provided with the capital letters M, N and P. A display 5 is also provided which indicates the time since medication was taken and/or the clock time which can be selected via a button 7. Finally, a removable chip 8 is shown which, as recording medium, contains the recorded values. The equipment is operated as follows. The patient who is wearing the equipment on his body, or is carrying it with him, first takes the medication prescribed by the doctor and at the same time pushes the button M. This starts up a stopwatch, i.e. the time begins to run at zero and is optionally shown on the display 5. If, after taking the medication, the patient now experiences a positive effect, he presses the P button 3. The equipment acknowledges that the button has been pressed by emitting an acoustic signal (beep) or an optical signal from a light 6, so that the patient receives confirmation of the entry he has made. If, after some time, the patient feels the effect is diminishing, he presses the N button 4. He then takes his medication for the second time as instructed by his doctor, and once again presses the M button 2, as a result of which the time is stored. The procedure described above is then repeated, i.e. pressing the P button when he experiences a positive effect and pressing the N button when he feels the effect diminishing. This is of course done in each case on the basis of the patient's subjective feelings.

Figure 2:
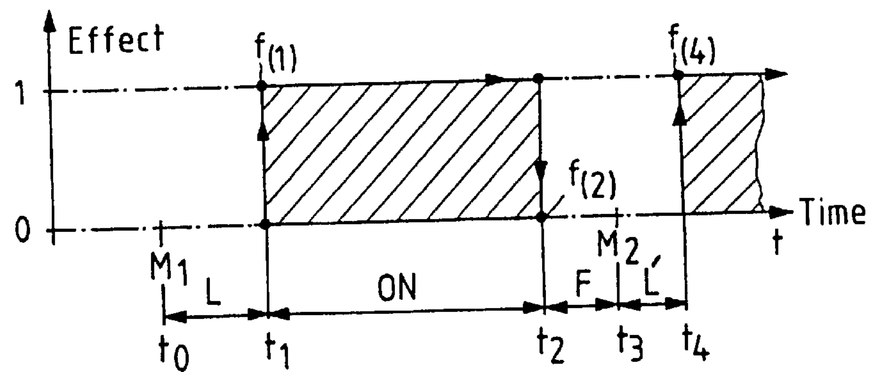
FIG. 2 shows a diagram of the function showing the change in effect over time, in the equipment according to FIG. 1.

The result of a single cycle of entries of this kind made by the patient is shown in the diagram according to FIG. 2. There, the positive effect of the medication is plotted on the ordinate over the time axis t, and only as a positive value of the order 1. The start of the measurement cycle upon administration of the medication is marked by the point $M_1$ on the abscissa, i.e. the time axis. Here, therefore, the effect of the medication is equal to 0. After some time, the so-called latency period L, the patient first experiences a positive effect and he presses the P button, as a result of which the value f(1)=1 is recorded at the time $t_1$. After a further time span, at the time $t_2$, the patient feels the effect diminishing or completely disappearing and he presses the N button, as a result of which the value f(2)=0 is recorded. The next time on the time axis is $M_2$, i.e. the time $t_3$, at which the medication is taken a second time. $M_2$ is recorded by pressing the M button; as can be seen, the effect of the medication is still zero at this time $t_3$, so that a so-called void time F occurs, i.e. a time span $t=t_3-t_2$ in which there is no effect of the medication. After the second administration of medication $M_2$, there is once again a latency period L', i.e. the time difference to the time $t_4$, at which the patient once again experiences a positive effect and presses the P button 3. This second latency period L' can be different than the first period L. The measurement cycle begun in this way can be continued as often as desired by repeated administration of the medication at the subsequent times $M_3, M_4, \ldots M_i$, with corresponding recording of the effect. The result is stored as a function according to the pattern in FIG. 2 and can be removed as a recording medium, e.g. on the chip. It would also be possible to analyze the stored function directly on a PC via a PC adapter, e.g. by comparing the effect profiles on different days, or to print out the stored function. This data, i.e. the effect function, helps the doctor to adopt a corrected or optimum medication program for the patient, and this with the goal of eliminating the abovementioned void times F and subsequent repeated latency periods L', i.e. the time spans in which there is no effect of the medication.

Figure 3:
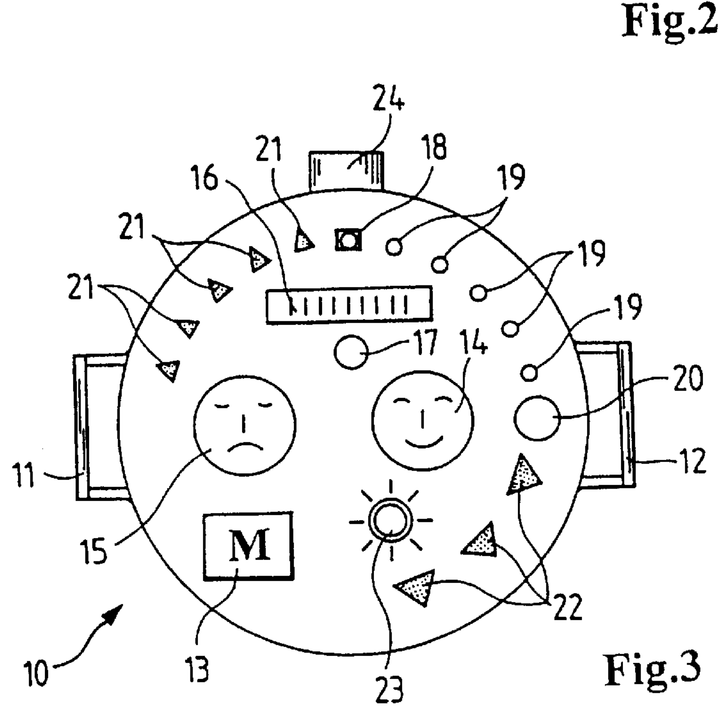
FIG. 3 shows an extended design of the recording equipment in the form of a wristwatch with optical display functions.

FIG. 3 shows a further illustrative embodiment of the invention, namely the recording equipment 10 in the form of a wristwatch with securing brackets 11 and 12 for a strap (not shown). The equipment 10, which is thus of essentially circular design in its plan view, has in the first place the M button 13 and the other buttons 14 and 15 for inputting a positive and a negative effect, the button 14 showing a laughing face and the button 15 showing a sad face. Moreover, a display 16 is provided for optionally displaying a running (stopwatch) time and the clock time, it being possible for the appropriate mode to be selected using the button 17. The equipment 10 also has five optical devices 19 (light-emitting diodes) which represent a respective recorded value. Five optical devices 21 (light-emitting diodes) are correspondingly provided on the left side of the circular equipment 10 for displaying the recorded negative effect. Between these two groups of five 19 and 21, a light arrangement 18 is provided for the zero setting, i.e. no effect. The equipment 10 also has a larger light arrangement 20 which is intended to signal an optimum for the patient's state of health. Finally, three further light arrangements 22 are provided for a so-called excess effect of the medication. The aforementioned groups of light arrangements are of different geometric designs and light up in different colors, e.g. group 19 and 20 in green, group 21 in blue and group 22 in yellow. Finally, an acoustic or optical signal arrangement 23 is provided in the area of the "clock face" of the equipment 10, which arrangement 23 emits acoustic or optical signals at the preprogrammed time for taking medication ($M_1$, $M_2$, $M_3$, etc.) in order to remind the patient to take the medication. The signal can also be generated by vibration. Finally, the equipment has a connection point 24 for an adapter (not shown) via which the stored data can be transferred to a PC and can be displayed on its screen.

Figure 4:
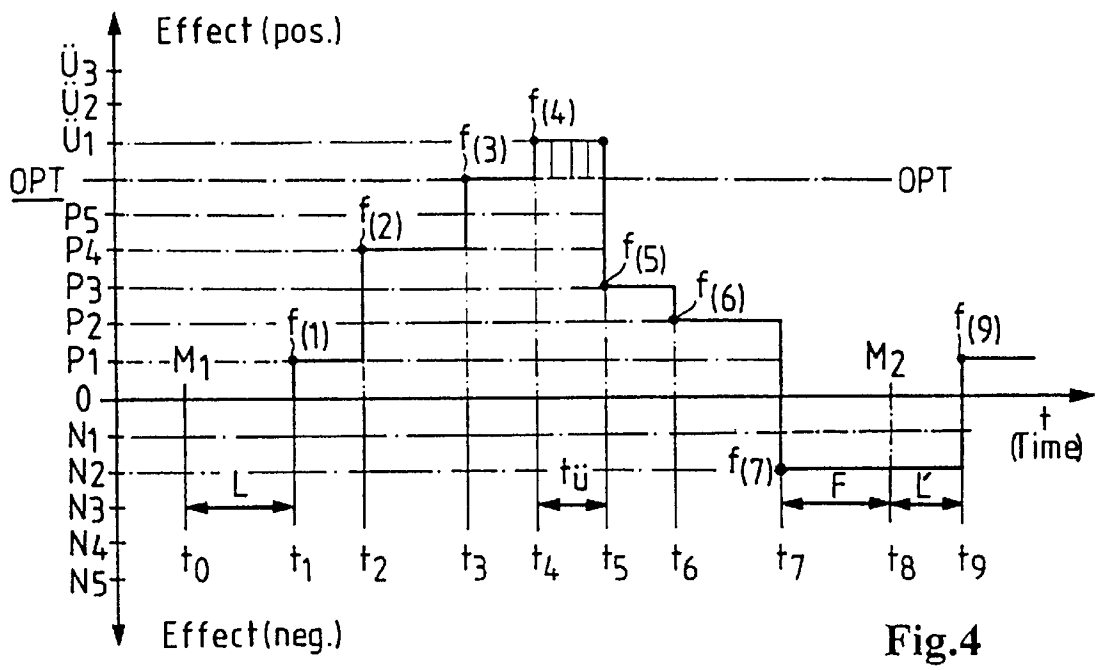
FIG. 4 shows a diagram of the stepped effect function of the equipment according to FIG. 3.

The function recorded and stored using the equipment 10 according to FIG. 3 is shown in the diagram in FIG. 4. Both the positive effect and the negative effect after taking medication are plotted over the time axis t, with five values P1 to P5 being provided for the positive effect and five values N1 to N5 for the negative effect. Above the value P5 there is a value OPT, representing the optimum, i.e. the best the patient feels, and above this there are three further values for an excess effect of the medication Ü1, Ü2, and Ü3. The diagram shown represents the variation in effect between the times at which medication was taken M1 and M2 and is recorded by pressing the buttons 13 (M), 14 for a positive effect and 15 for a negative effect. The measurement cycle begins at the time $t_0$ at which the patient presses the button M or 13 on first taking the medication. After the latency period L has elapsed, he experiences a first positive effect and presses the button 14 once at the time $t_1$, as a result of which the value f(1), corresponding to the value P1, is recorded on the positive ordinate. At the time $t_2$ the patient experiences an increasing positive effect which he assesses subjectively with the value P4, and for this he has to press the button 14 three times in succession, which results in a jump from P1 to P4 to the value f(2). When the value P1 is recorded, the first light arrangement 19 lights up (green), and when the value P4 is recorded three further light arrangements 19 light up, that is to say altogether four light arrangements 19 are lit. At the time $t_3$ the patient experiences an optimum effect and presses the button 14 again, as a result of which he reaches the value P5, and by pressing the button 14 one more time the value OPT, i.e. the optimum, corresponding to f(3) is reached, and at the same time a larger light arrangement 20 lights up (green). The patient thus sees that the optimum effect of the medication has now been recorded. At the time $t_4$ he experiences an excess effect of the medication and therefore presses the button 14 once again, as a result of which the value f(4), corresponding to Ü1, is recorded on the ordinate. When the value Ü1 is reached, i.e. recording of an excess effect, the further light arrangement 22 lights up (yellow), thus optically signalling the range of the excess effect. If the patient feels this excess effect diminishing, he can press the button 15, as a result of which, if the latter is pressed once, the value OPT (optimum) is once again reached. If the effect further diminishes, the patient can once again press the button 15—one unit is subtracted for each single actuation. In the case shown, by pressing the button 15 four times, he reaches the value P3 at the time $t_5$, corresponding to f(5), and by pressing it again he reaches the value P2 at the time $t_6$, corresponding to f(6). At the time t7 the patient experiences a greatly diminishing effect, dropping into the negative range. He therefore presses the button 15 four times and reaches the negative value f(7) corresponding to N2. At the same time, two light arrangements 21 now light up (blue); five light-emitting diodes 21 (blue) are provided corresponding to the negative scale of values N1 to N5. The next time $t_8$ corresponds to the planned time M2 for taking the second dose of the medication. In this case, therefore, there is still a negative effect of the medication which lasts until the time $t_9$: only then does the patient experience a positive effect again, and he presses the button 14 with the laughing face three times and reaches the value f(9) which corresponds to the value P1 on the ordinate. The time span between $t_8$ and $t_7$ corresponds to the void time F in which there is no positive effect of the medication, and the time span between $t_9$ and $t_8$ is the second latency period L' after taking the second dose of medication. Thereafter, the measurement cycle is continued as described above. The groups of light-emitting diodes 19 to 22 can each have different colors (as indicated above) or can light up in the same color but with different brightness or with a different contour (if the patient is color-blind). This diagram, which can be stored on a recording medium or can be transferred to a PC via an adapter, is used by the doctor as a basis for more accurately adapting the medication, i.e. on the one hand in terms of the choice of times M1, M2, M3 etc., and also in terms of the dose of the medication. The latter can be adapted, for example, if an excess effect occurs—in this case up to the value Ü1 over the time $t_{ü}$—since in this case the dose of the medication was too strong.

Figure 5:
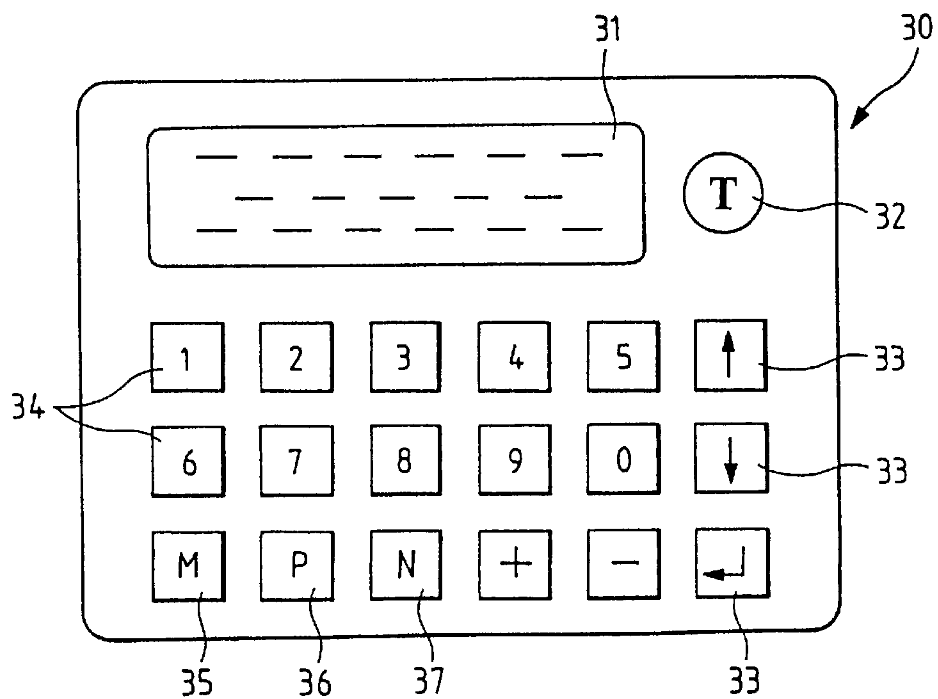
FIG. 5 shows a further design of the recording equipment with extended input functions.

FIG. 5 finally shows a further design of the invention, namely in the form of equipment 30 which has an enlarged display or a small screen 31, a keyboard 33, 34 and the already described buttons with capital letters M, P and N corresponding to reference numbers 35, 36, 37. In addition, a time switch 32 with the capital letter T is provided which makes it possible to switch alternately between stopwatch and clock time. The buttons 34 with the numbers 1, 2, 3 through 0 correspond to side effects, e.g. headache, nausea, fever or tachycardia. Thus, by using the keyboard, the patient is able to call up on screen the side effect which occurs after he takes the medication and to record the time at which it occurred. In addition to entering side effects, it is also possible to select on the equipment specific symptoms which are intended to be influenced by the medication, e.g. tremor (trembling of body parts), muscle mobility, anxiety or agitation, to assess these and to record the time at which they occurred. In this way, different effect profiles can be stored in parallel. Finally, the program of this equipment 30 makes it possible to record the effect of combinations of medication, that is to say several medications taken concurrently.

Figure 6:
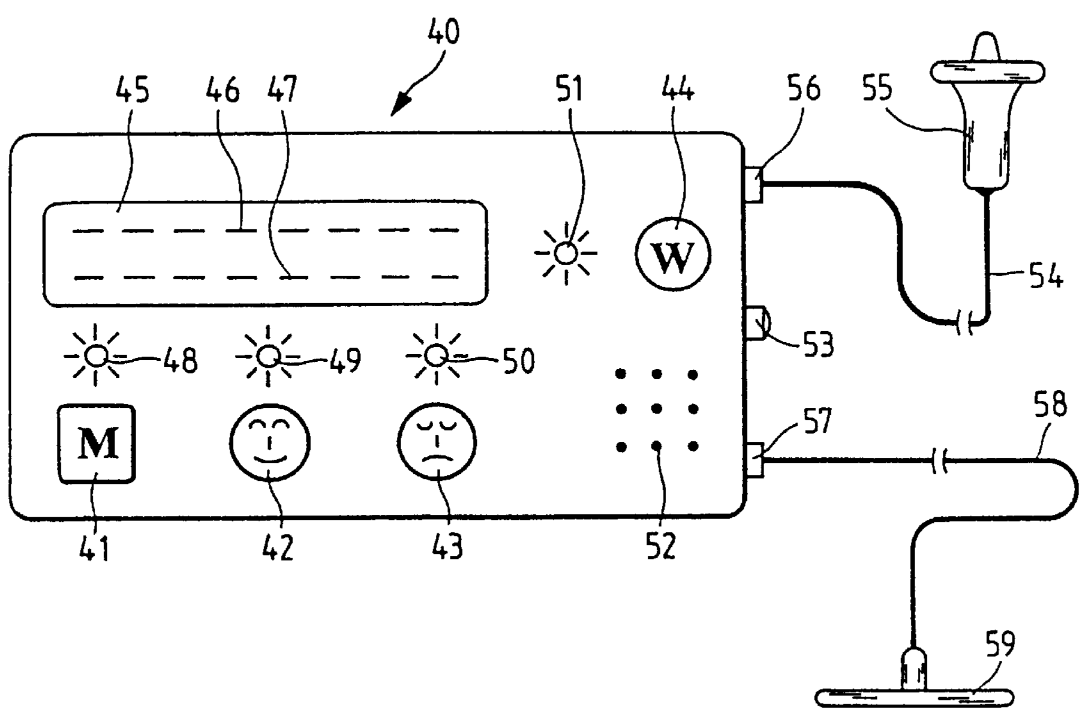
FIG. 6 shows a further design of the recording equipment with external key switch and external sensor.

FIG. 6 shows a further embodiment of the equipment according to the invention with expanded mode for superposed recording of additional events and symptoms of the disease and their assessment. The equipment 40, like equipment 1 and 10, has three buttons which correspond to the buttons M, N and P or 13, 14 and 15, i.e. the button 41 with the letter M is intended for entering the time at which the medication is taken, the button 42 with the laughing face is intended for entering a positive effect or assessment and the button 43 with the sad face is intended for entering a negative effect or assessment. A button 44 with the letter W is also provided by means of which certain events and symptoms of certain diseases can be called up on a two-line display 45 and displayed. For example, various main terms such as tremor, mobility, headache, nausea or anxiety can be called up and displayed in the top line 46 of the display 45 by actuating the button 44 (W). A possible assessment of the corresponding event then appears in the bottom line 47. By actuating the button 42 or 43, an assessment can then be made in different stages, e.g. for headaches:

| | |
|---|---|
| no headache | (0) |
| very slight headache | (1) |
| mild headache | (2) |
| moderate headache | (3) |
| severe headache | (4) |
| very severe headache | (5) |

Such an assessment is not made in response to a request, but when the patient feels it necessary. The event and its assessment are thus superposed on the recording of the abovementioned effect of the medication according to FIG. 2 and FIG. 4. The doctor is thus provided with additional information which allows him to make an accurate assessment of the effect of the medication. For visual confirmation of the individual entries made using the buttons 41, 42, 43 and 44, these are each assigned colored lights 48, 49, 50 and 51 which light up when an entry is made, namely in yellow (48), green (49), red (50) and blue (51). The equipment 40 also has a small speaker 52 via which certain entries receive an audible spoken confirmation, e.g. via the speaker the equipment 40 "says" the following words or phrases: "Administration of medication recorded" or "Effect of medication now: slight improvement". A push switch 53 is also arranged on the equipment 40 and is used to switch the speaker 52 on and off.

A key switch 55 which can be operated by the patient can be connected to the equipment 40 via a cable 54 and connection socket 56, and entries can be made using this key switch 55 in addition to the buttons 42 and 43. This key switch 55 represents, as it were, a remote control for the equipment 40 in some cases: for example, by pressing the key switch 55, it is possible to record additional and sudden events along with their clock time, without the patient having to take the equipment 40, which he carries with him, out of his pocket. This is particularly advantageous for patients with Parkinson's disease in the so-called off-phase, because the patient is at that time severely restricted in his movements. Also in the case of anxiety attacks or other sudden and critical changes in the state of health, e.g. absences in epileptics, the immediate activation of the key switch 55 permits immediate recording of this event. The key switch 55, however, can also be used as an alternative to the input buttons 42 and 43, in other words for entering a positive or negative effect of the medication. For this purpose, a code can be used which is easily understood by the patient: e.g. a short press on the key switch 55 would mean that there was no effect of the medication, and a long press on the key switch 55 would mean that there was a positive effect. This remote entry via the key switch 55 can then be confirmed acoustically via the speaker 52 of the equipment 40, so that the patient knows what has been recorded. Alternatively, confirmation by means of vibration is also possible.

Finally, the equipment 40 also has an attachment 57 for diverse sensors or measurement equipment via which physically measurable data from the patient are recorded. Here, by way of example, a measurement sensor 59, shown diagrammatically, is connected via a cable 58 and is used to measure the patient's heart rate. Alternatively, or in addition to this, further measurement sensors can be connected, for example for measuring the blood pressure, blood oxygen or blood sugar levels, tremor, muscle tone (muscular tension) and skin temperature or skin moisture. These objectively measurable values can be measured and recorded automatically, without the assistance of the patient, and can be stored on the abovementioned recording medium and output. In this respect it is possible, with this combination of equipment 40, for the subjective state of health after medication and the objectively determined physiological values to be recorded and stored in parallel. This represents a considerable therapeutic aid to the doctor and an improvement to the patient's medication.

The drawing does not show a combination of the above-described equipment with a medication dispenser containing the prescribed medication in a quantity suitable for a defined period. At the preset times $M_1$, $M_2$, $M_3$ etc. which are stored in the equipment, the medication dispenser opens and supplies the prescribed dose of medication, i.e. the patient can then remove the medication. At the same time, the above-described signal or alarm arrangement can activate and thus remind the patient to take the medication. The medication to be taken at this time can be displayed, e.g.:

"½ tablet of Madopar 125 T".

As has already been mentioned above, the equipment according to the invention is not only intended for use where a patient is being treated with medication by a doctor, but can also be used, for example, in pharmaceutical research when new active substances, remedies, drugs or the like are being tested and evaluated for their effect on the human body.

I claim:

1. A portable device for recording, displaying and storing values concerning a patient's subjective state of health, comprising:

a first button for recording a time ($t_0$) at which medication was taken, a second button for recording a positive effect and a time ($t_1$) at which the positive effect is perceived, a third button for recording a negative effect and a time ($t_2$) at which the negative effect is perceived, and a recording medium which stores values input with the first, second, and third buttons.

2. A portable device according to claim 1, wherein the recording medium is removable.

3. A portable device according to claim 1, further comprising an interface for a PC adapter through which the stored values can be transferred to a PC.

4. A portable device according to claim 1, further comprising a visual display for displaying information based on the values stored on the recording medium.

5. A portable device according to claim 4, wherein the visual display displays an elapsed amount of time measured from the time to at which medication was taken.

6. A portable device according to claim 5, wherein the visual display displays a time of day.

7. A portable device according to claim 4, wherein the visual display displays a state of the patient's health determined from the values stored on the recording medium.

8. A portable device according to claim 4, further comprising a fourth button and a visual display, said fourth button activating the visual display.

9. A portable device according to claim 1, further means to confirm entry of values with one of the first, second or third buttons acoustically, by touch, or visually.

10. A portable device according to claim 1, wherein the device is adapted to be worn around the patient's wrist.

11. A portable device according to claim 1, further comprising a keyboard for recording side effects or feelings experienced by the patient.

12. A portable device according to claim 1, wherein the device is connected to a medication dispenser which contains medication that is dispensed at preset times in an appropriate dose.

13. A portable device according to claim 1, wherein the values input with the second and third buttons correspond to relative values indicative, respectively, of whether the patient perceives that the patient feels better or worse than at a previous time that occurred after the medication was taken.

14. A portable device according to claim 1, wherein the values input with the second and third buttons are recorded as a function of time elapsed since the medication was taken.

15. A portable device for recording, displaying and storing values concerning a patient's subjective state of health, comprising:

a first button for recording a time ($t_0$) at which medication was taken, a second button for recording a positive effect and a time ($t_1$) at which the positive effect is perceived, a third button for recording a negative effect and a time ($t_2$) at which the negative effect is perceived, a recording medium which stores values input with the first, second, and third buttons, and a speech module with a speaker which provides an audible spoken confirmation of each entry made with said first, second, or third button.

16. A portable device for recording, displaying and storing values concerning a patient's subjective state of health, comprising:

a first button for recording a time ($t_0$) at which medication was taken, a second button for recording a positive effect and a time ($t_1$) at which the positive effect is perceived, a third button for recording a negative effect and a time ($t_2$) at which the negative effect is perceived, a recording medium which stores values input with the first, second, and third buttons, and a key switch, whereby information can be input manually with the key switch.

17. A portable device for recording, displaying and storing values concerning a patient's subjective state of health, comprising:

a first button for recording a time ($t_0$) at which medication was taken, a second button for recording a positive effect and a time ($t_1$) at which the positive effect is perceived, a third button for recording a negative effect and a time ($t_2$) at which the negative effect is perceived, a recording medium which stores values input with the first, second, and third buttons, and a plurality of optical display devices which display recorded values corresponding to positive, negative, excess, or optimum perceived medication effect.

18. A portable device for recording, displaying and storing values concerning a patient's subjective state of health, comprising:

a first button for recording a time ($t_0$) at which medication was taken, a second button for recording a positive effect and a time ($t_1$) at which the positive effect is perceived, a third button for recording a negative effect and a time ($t_2$) at which the negative effect is perceived, a recording medium which stores values input with the first, second, and third buttons, and a sensor for detecting and recording physically measurable physiological values of the patient.

19. A portable device for recording, displaying and storing values concerning a patient's subjective state of health, comprising:

a first button for recording a time ($t_0$) at which medication was taken, a second button for recording a positive effect and a time ($t_1$) at which the positive effect is perceived, a third button for recording a negative effect and a time ($t_2$) at which the negative effect is perceived, and a recording medium which stores values input with the first, second, and third buttons, and stores preset times at which medication is to be taken.

20. A portable device according to claim 19, further comprising a speaker which provides an audible indication of the preset times at which medication is to be taken.

21. A portable device according to claim 19, further comprising visual indicators which provide indications of the preset times at which medication is to be taken.

22. A portable device according to claim 19, wherein the device vibrates at the preset times at which medication is to be taken.

23. A portable device according to claim 19, wherein the device is connected to a medication dispenser which contains medication that is dispensed in an appropriate dose at the preset times.

* * * * *